US009351641B2

(12) United States Patent
Neff

(10) Patent No.: US 9,351,641 B2
(45) Date of Patent: May 31, 2016

(54) MOBILE PROCESSING DEVICE SYSTEM FOR PATIENT MONITORING DATA ACQUISITION

(71) Applicant: Cerner Innovation, Inc., Kansas City, KS (US)

(72) Inventor: Robert A. Neff, Villanova, PA (US)

(73) Assignee: Cerner Innovation, Inc., Kansas City, KS (US)

(*) Notice: Subject to any disclaimer, the term of this patent is extended or adjusted under 35 U.S.C. 154(b) by 447 days.

(21) Appl. No.: 13/743,731

(22) Filed: Jan. 17, 2013

(65) Prior Publication Data

US 2014/0098209 A1    Apr. 10, 2014

Related U.S. Application Data

(60) Provisional application No. 61/709,462, filed on Oct. 4, 2012.

(51) Int. Cl.
| H04N 9/47 | (2006.01) |
| H04N 7/18 | (2006.01) |
| A61B 5/00 | (2006.01) |
| G06K 9/32 | (2006.01) |

(52) U.S. Cl.
CPC ............ *A61B 5/0033* (2013.01); *G06K 9/3258* (2013.01); *A61B 5/743* (2013.01); *G06K 2209/03* (2013.01)

(58) Field of Classification Search
USPC ......... 348/77, 49, 50, 63, 135, 130, 136, 158, 348/180, 231.3, 376, 468, 583, 714, 715, 348/838; 382/282, 286, 289, 295, 296, 302; 600/424, 438, 300, 301, 483; 705/2, 3
See application file for complete search history.

(56) References Cited

U.S. PATENT DOCUMENTS

| 8,924,878 B2* | 12/2014 | Palmer et al. ................ 715/771 |
| 2002/0049371 A1* | 4/2002 | Lai ........................ A61B 5/0205 600/300 |
| 2002/0091548 A1* | 7/2002 | Auer et al. ....................... 705/3 |
| 2004/0024615 A1* | 2/2004 | Monteleone et al. ............. 705/2 |
| 2004/0153965 A1* | 8/2004 | O'Rourke .................... 715/505 |
| 2007/0094052 A1* | 4/2007 | Blas ............................... 705/3 |
| 2008/0077436 A1* | 3/2008 | Muradia .......................... 705/2 |

(Continued)

OTHER PUBLICATIONS

Kirill Safronov, "Optical Character Recognition Using Optimisation Algorithms", Workshop on Computer Science and Information Technologies CSIT'2007, Ufa, Russia, 2007.

*Primary Examiner* — Jefferey Harold
*Assistant Examiner* — Mustafizur Rahman
(74) *Attorney, Agent, or Firm* — Shook, Hardy & Bacon L.L.P.

(57) ABSTRACT

A mobile processing device system for patient monitoring data acquisition includes a repository of information. The information associates a particular patient monitoring device type for displaying a particular patient parameter with a particular text label identifying the particular patient parameter. A portable processing device includes an imaging device for acquiring image data representing an image presenting patient parameter data from the particular patient monitoring device type. An image recognition processor, uses the information, for analyzing the image data to identify the particular text label identifying the particular patient parameter and a value of the particular patient parameter. An output processor communicates data representing the particular patient parameter and the value to a destination.

20 Claims, 8 Drawing Sheets

(56) References Cited

U.S. PATENT DOCUMENTS

| | | | |
|---|---|---|---|
| 2008/0091470 A1* | 4/2008 | Muradia | 705/3 |
| 2008/0281168 A1* | 11/2008 | Gibson et al. | 600/301 |
| 2009/0213213 A1* | 8/2009 | Fright et al. | 348/77 |
| 2009/0216112 A1* | 8/2009 | Assis et al. | 600/424 |
| 2012/0022348 A1 | 1/2012 | Droitcour et al. | |
| 2012/0045790 A1* | 2/2012 | Van Dijk et al. | 435/29 |
| 2012/0218404 A1 | 8/2012 | Buxton et al. | |
| 2013/0109929 A1* | 5/2013 | Menzel | G06F 19/3406 600/301 |

* cited by examiner

MOBILE PROCESSING DEVICE SYSTEM FOR PATIENT MONITORING DATA ACQUISITION

This is a non-provisional application of provisional application Ser. No. 61/709,462 filed Oct. 4, 2012, by R. Neff.

FIELD OF THE INVENTION

This invention concerns a mobile processing device using an image recognition processor for analyzing acquired image data representing an image presented on patient monitoring equipment, to identify a particular text label identifying a particular patient parameter and a value of the particular patient parameter.

BACKGROUND OF THE INVENTION

Known patient data acquisition systems utilize different hardware and software features (wireless data transmitters, software device drivers, for example) to connect to a patient monitoring device. The Known patient data acquisition systems also use different communication methods to acquire data from patient monitoring devices. However, the known patient data acquisition systems typically support a limited set of devices and infrastructure to setup and configure the devices for communication. Additionally, known methods typically require a cumbersome workflow and additional hardware. A system according to invention principles addresses these deficiencies and related problems.

SUMMARY OF THE INVENTION

A mobile device system uses a camera on the mobile device to visually capture and transcribe vital sign data to text, for example, from a patient monitor and send the text data to a healthcare information system (HIS). A mobile processing device system for patient monitoring data acquisition includes a repository of information. The information associates a particular patient monitoring device type for displaying a particular patient parameter with a particular text label identifying the particular patient parameter. A portable processing device includes an imaging device for acquiring image data representing an image presenting patient parameter data from the particular patient monitoring device type. An image recognition processor, uses the information, for analyzing the image data to identify the particular text label identifying the particular patient parameter and a value of the particular patient parameter. An output processor communicates data representing the particular patient parameter and the value to a destination.

DETAILED DESCRIPTION OF THE INVENTION

A system according to invention principles uses a camera on a mobile device to collect and transcribe vital sign and other patient data to text. The vital sign and patient data is acquired from a patient monitor and sent to an HIS (Healthcare Information system). Patient and vital sign data is captured quickly and efficiently from a medical device displaying the data without a connection to that device using a camera on the mobile device (phone or tablet, for example). In one embodiment the system also uses a barcode reader (or a camera image of a barcode) for patient selection to streamline the workflow.

Figure 1:
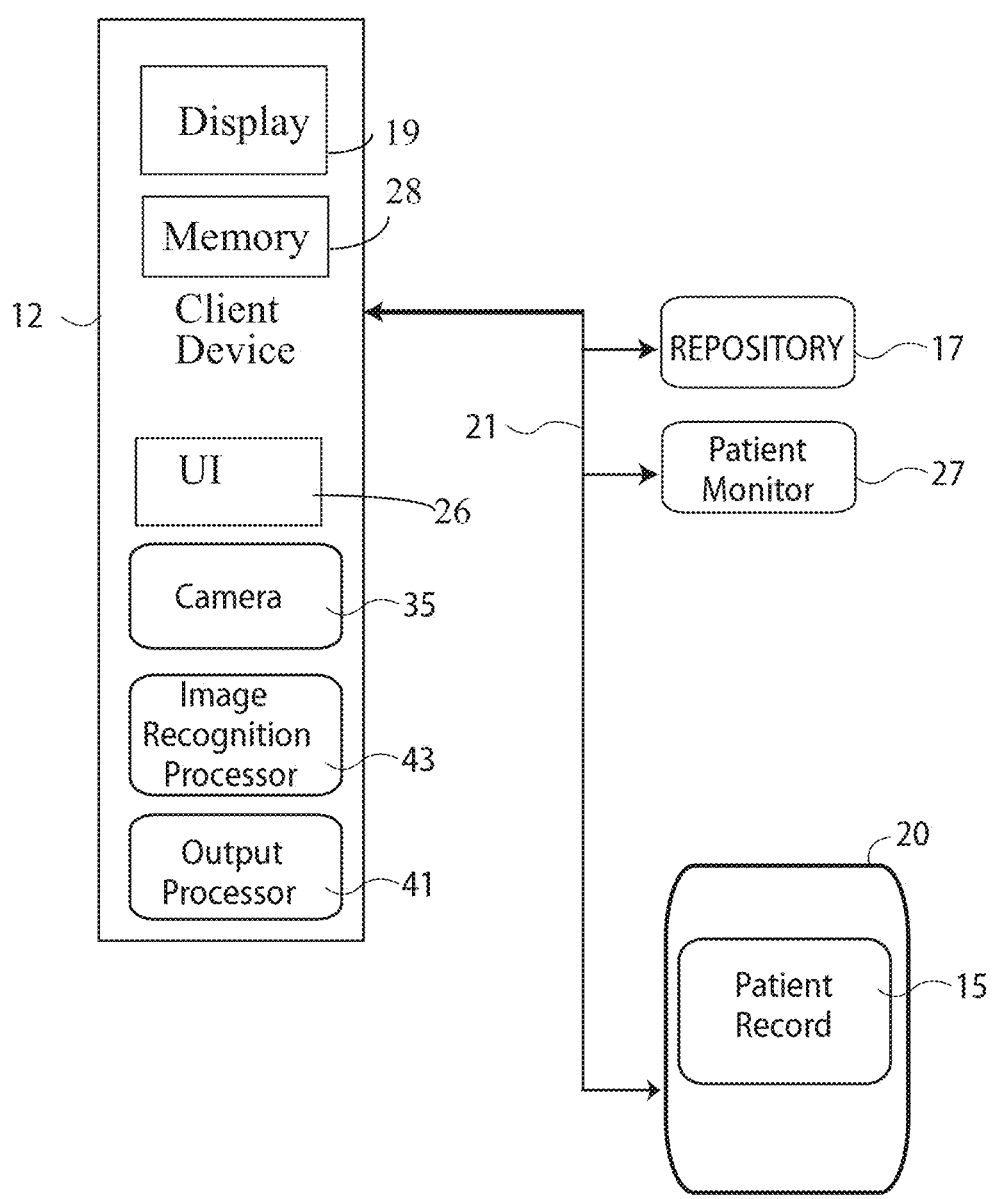
FIG. 1 shows a mobile processing device system for patient monitoring data acquisition, according to an embodiment of the invention.

FIG. 1 shows a mobile processing device system 10 for acquiring data from patient monitor 27. System 10 includes portable processing device (computer) 12, at least one repository 17, patient monitor 27 and server 20. Portable processing device 12 bidirectionally communicates with server 20, repository 17, patient monitor 27 and server 20. Portable processing device 12 includes memory 28, a user interface 26 enabling user interaction with a Graphical User Interface (GUI) and display 19 supporting GUI and medical data, image and administrative information presentation in response to predetermined user (e.g., physician, nurse administrator) specific preferences. At least one repository 17 stores information associating a particular patient monitoring device type for displaying a particular patient parameter with a particular text label identifying the particular patient parameter. Portable processing device 12 includes an imaging device (e.g. camera 35, or a bar or Quick Response code reader) for acquiring image data, representing an image presenting patient parameter data, from the particular type of patient monitoring device 27. Image recognition processor 43, uses the information, for analyzing the image data to identify the particular text label identifying the particular patient parameter and a value of the particular patient parameter. Output processor 41 communicates data representing the particular patient parameter and the value to a destination comprising patient record 15 in server 20.

Repository 17 further stores information that associates particular patient monitoring device type with a particular image type displayed by a device type and with a particular text label identifying the particular patient parameter presented in the particular image type and with a particular area location mask in the particular image type. The information also associates the particular patient monitoring device type with a version identifier and a manufacturer identifier and associates the particular patient monitoring device type with particular text labels including at least two of, HR, RR, NIBP, TEMP (TEMPERATURE), for example.

Figure 2:
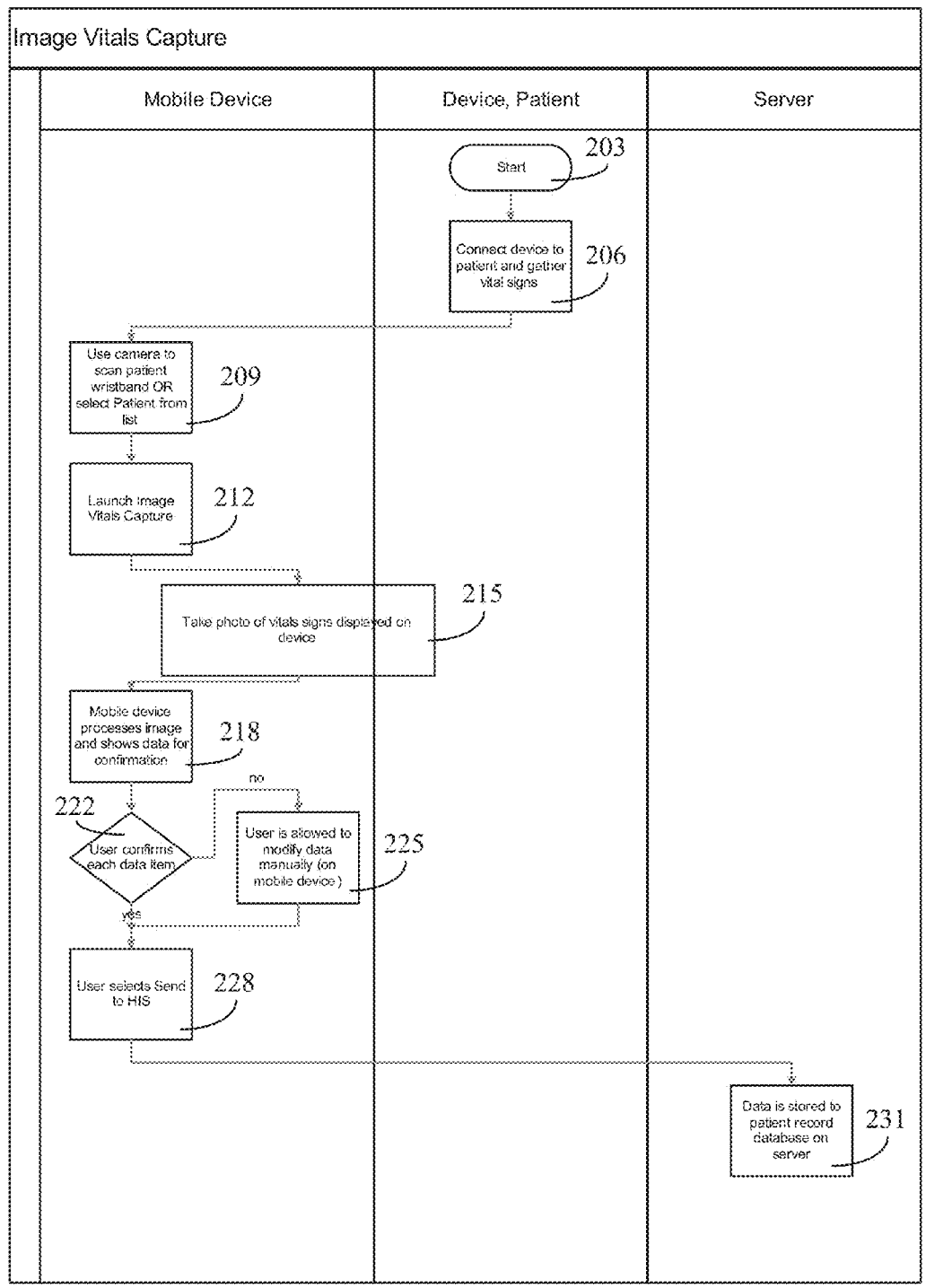
FIG. 2 shows a flowchart of a workflow process employed by a mobile processing device system for patient monitoring data acquisition, according to an embodiment of the invention.
Figure 3:
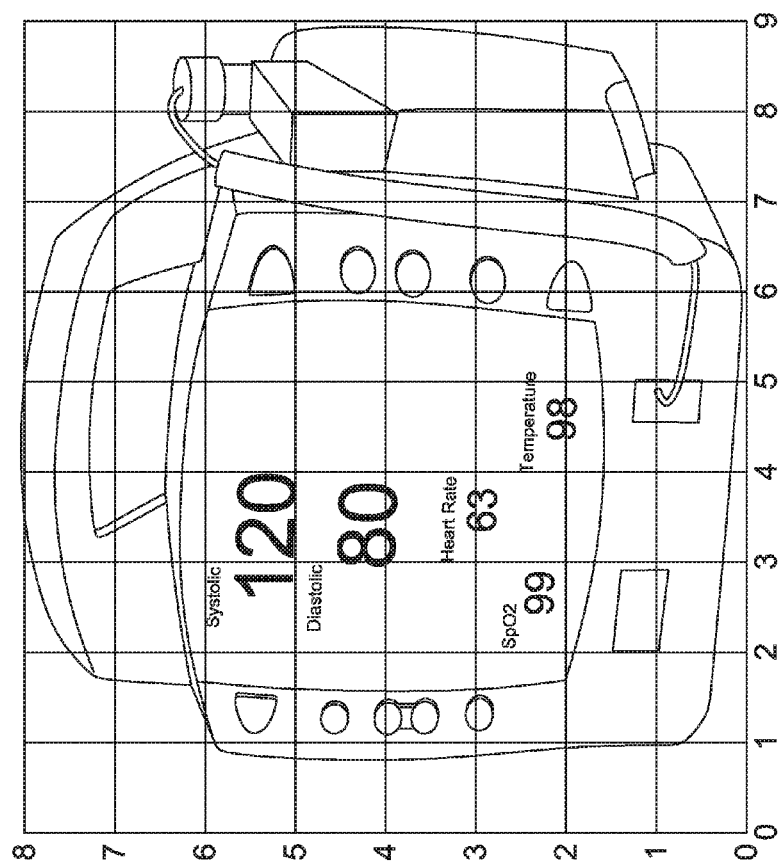
FIG. 3 shows a patient monitoring device and mask grid, according to an embodiment of the invention.
Figure 4:
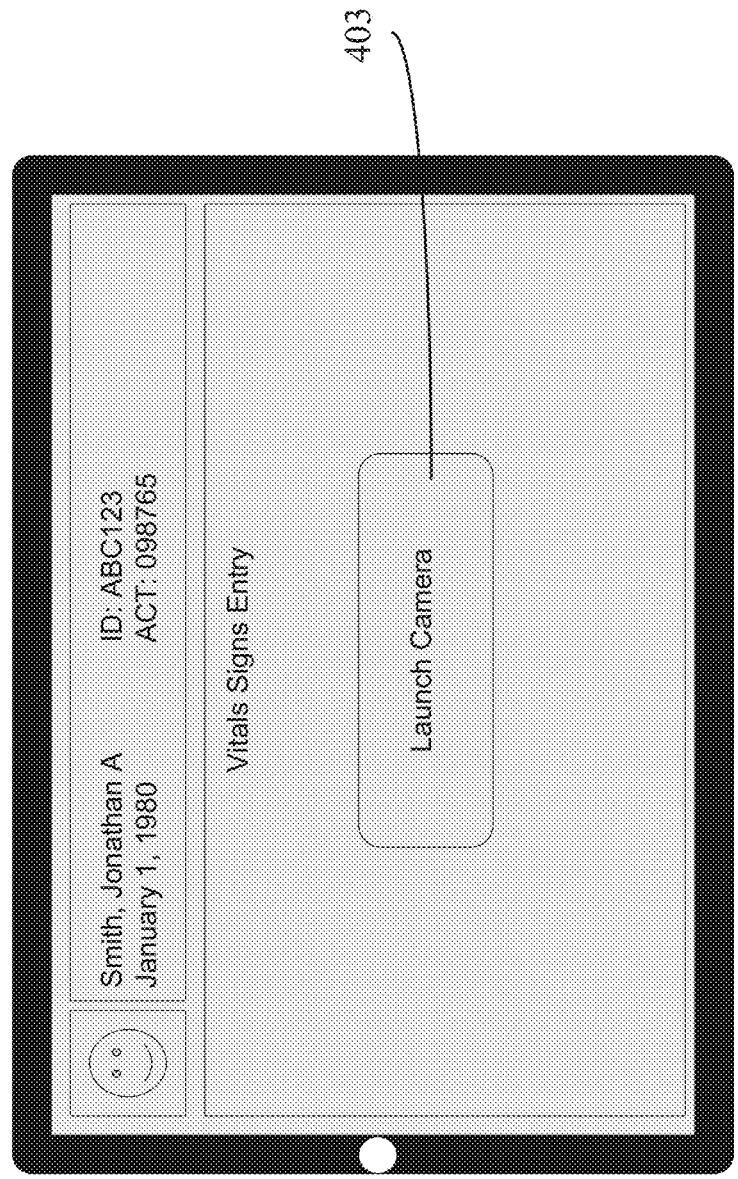
FIG. 4 shows a mobile processing device display image for initiating image capture, according to invention principles.

FIG. 2 shows a flowchart of a workflow process employed by a mobile processing device system for patient monitoring data acquisition. In step 206 following the start at step 203, patient monitoring device 27 is attached to a patient. FIG. 3 shows a patient monitoring device and mask grid. A user in step 209 selects a patient from a displayed list using user interface 26 or uses camera 35 in device 12 to scan a patient identification bar code on a wrist band to identify a patient, for example. In step 212 a user initiates execution of an image capture executable application. FIG. 4 shows a mobile processing device display image presented on display 19 of portable device 12 and enabling a user to initiate an image capture application via button 403.

In step 215, a user initiates acquisition of an image of patient parameters comprising vital signs displayed by a particular type of monitor (patient monitor 27) using camera 35 and the image capture application. In step 218 image recognition processor 43 uses information stored in repository 17, for analyzing the acquired image data to identify a particular text label identifying a particular patient parameter and a value of the particular patient parameter. Processor 43 recognizes patient monitoring device data using image recognition and OCR (Optical Character Recognition) functions for recognizing displayed text presented on the device.

Figure 5:
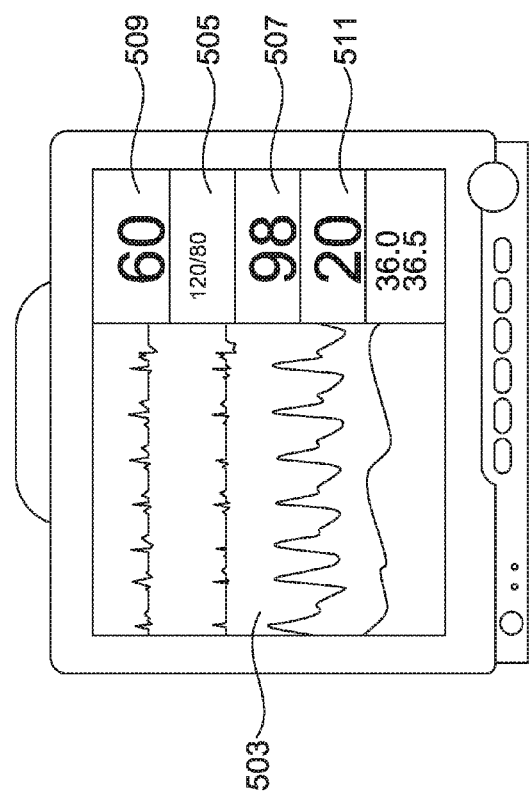
FIG. 5 shows a patient monitor display image.

FIG. 5 shows patient monitor 27 presenting display image 503. Processor 43 recognizes displayed text presented in image 503 as well as separators of the text on the screen. The separators include boxes, lines and colors, for example, as shown in image 503 which differentiate one measurement from another. Non-invasive blood pressure (NIBP) 505 is separated from blood oxygen saturation (SPO2) 507 by lines distinguishing the boxes containing pressure 505 and SPO2 507. These values are further differentiated by the different colors in which the pressure and SPO2 values are presented, for example. Image 503 shows heart rate (HR) 509, RR wave interval 511, NIBP 505, and SPO2 507 values in respective distinct boxes with identifying label and value. Processor 43 is preconfigured to acquire a set of specific values it is looking for in particular images of particular types of devices and their different versions. These specific values are stored in a library including HR, RR, NIBP, TEMP (TEMPERATURE), for example. The library advantageously limits the amount of processing that needs to be done, and also prevents the system from acquiring text which is not clinical data (for example labels on the screen which say "settings" or "mode"). Processor 43 processes images acquired by camera 35 using information in repository 17 associating a particular image of multiple different images of a version of an individual patient monitoring device of a particular manufacturer with labels used on the device image (e.g. predetermined labels HR, RR, NIBP, TEMP (TEMPERATURE)) and with predetermined image locations at which labels are expected. The information includes such particular image data and associations for a library of device types and device models and versions. Processor 43 recognizes a particular image of a particular device by matching with predetermined template images or features based on image object comparison using iterative transformations including scaling, translation and rotation transformations to recognize matching objects and features to identify an image. The library maps location of information in an image of a particular recognized image of a particular device of multiple different devices, so specific areas of the image may be examined in more detail by processor 43. This improves accuracy of identification of data on a displayed image, specifically on devices in which it is difficult to determine which value displayed is for which physiological parameter.

Figure 7:
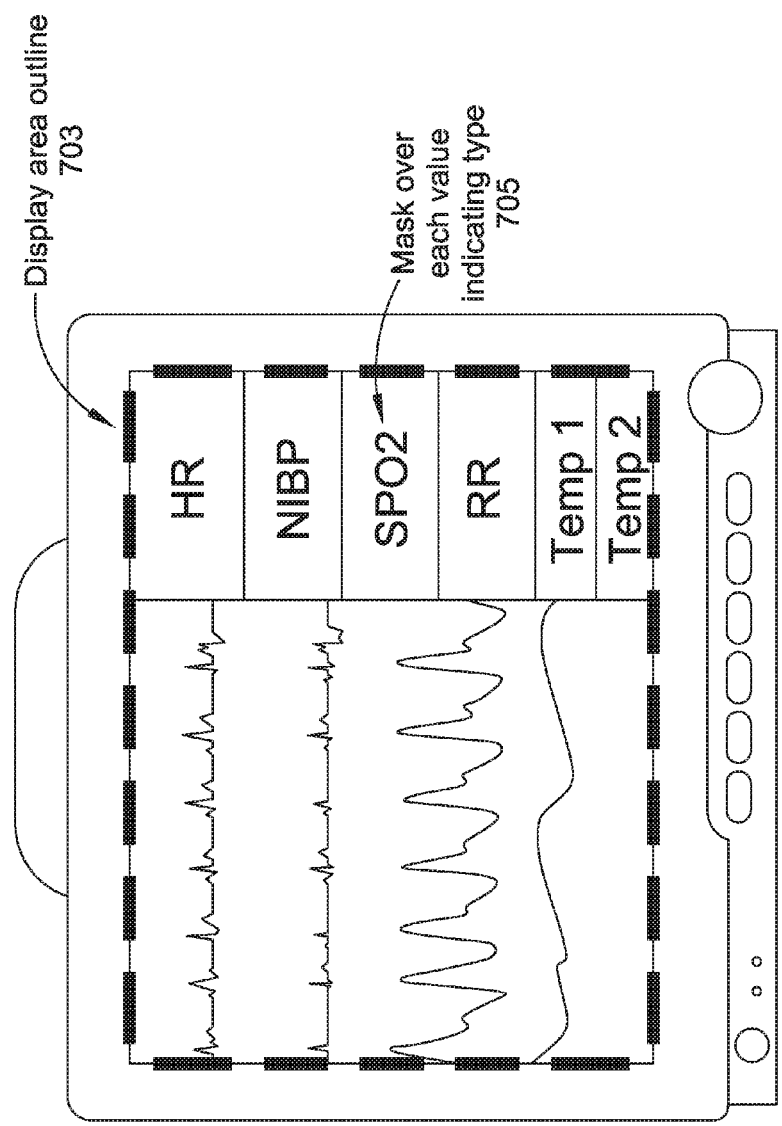
FIG. 7 shows a patient monitor display image illustrating a monitoring device specific mask used for facilitating image capture and patient parameter data recognition, according to an embodiment of the invention.

FIG. 7 shows a patient monitor display image within outline 703 illustrating a monitoring device specific mask (map) used for facilitating image capture and patient parameter data recognition. Information in repository 17 includes a mask facilitating processing data from patient monitor 27. Processor 43 uses a mask for a specific image of multiple different images of a particular type of patient monitor device of a particular version and manufacturer that matches an outline of a display area of an acquired image. A monitoring device 27 image and associated mask stored in repository 17 are recognized based on matching predetermined reference features of the mask with corresponding features having corresponding locations in an image displayed by device 27 using iterative rotation, scaling and translation transformations that fit the mask to the image. Processor 43 further uses the identified reference features and the geometry of the mask to identify locations on the image where parameters such as SPO2 705 and HR, RR, NIBP, for example, and associated parameter labels are expected to be located to facilitate text recognition using OCR.

Figure 6:
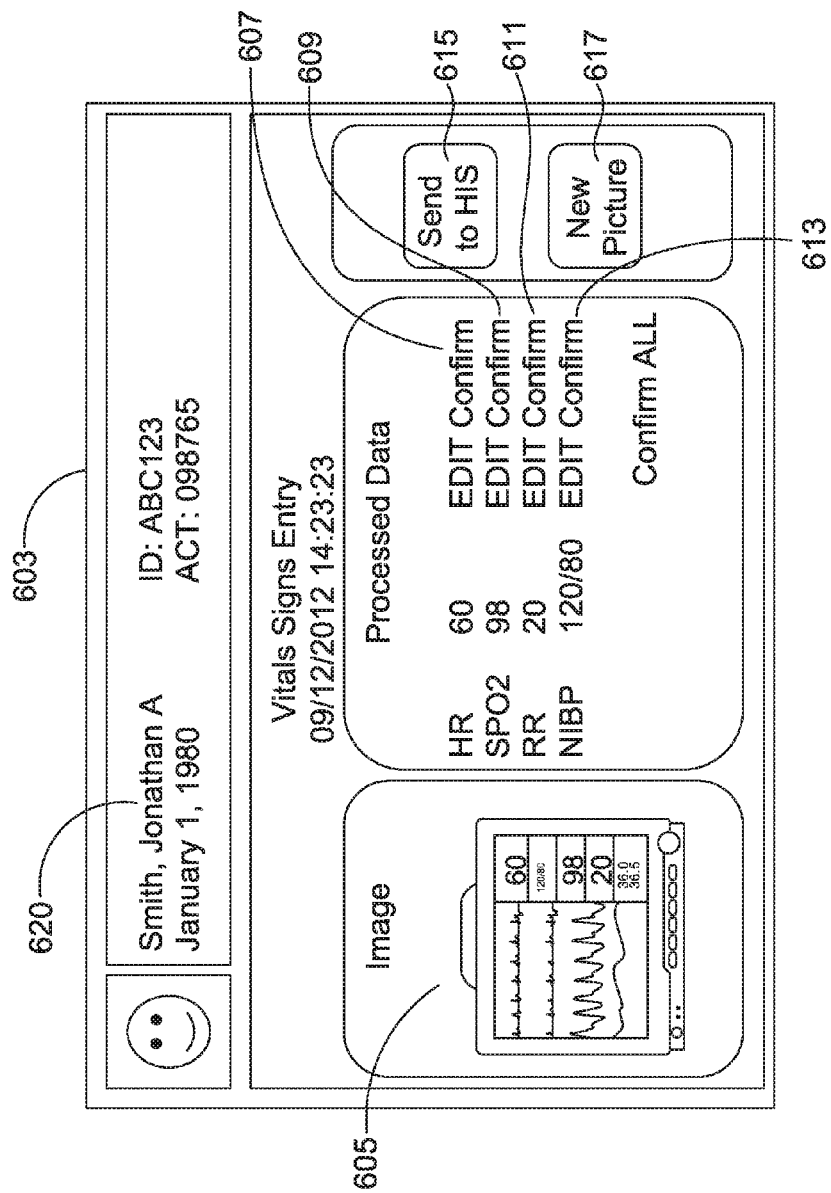
FIG. 6 shows a mobile processing device display presenting a captured patient monitor image and associated recognized patient parameter data enabling a user to edit or confirm recognized data and communicate recognized data, according to invention principles.

Further, in step 218, image recognition processor 43 recognizes the text in the masked areas by using the mask information stored in repository 17, for analyzing the acquired image data to identify a particular text label identifying a particular patient parameter and a value of the particular patient parameter. Processor 43 recognizes patient monitoring device data including parameter labels and values using image recognition and OCR (Optical Character Recognition). Output processor 41 displays data representing parameter labels and values in image 603 of FIG. 6 presented on display 19. FIG. 6 shows mobile processing device display image 603 presenting a captured patient monitor image and associated recognized patient parameter data enabling a user to edit or confirm recognized parameter data and communicate recognized data. Parameters HR, SPO2, RR, NIBP are shown in rows 607, 609, 611 and 613 respectively together with image elements enabling a user to edit or confirm the data. The corresponding patient monitoring device 27 image from which the parameters are automatically recognized is shown in reduced size in area 605 adjacent to the recognized parameters. The patient and date concerned is shown in area 620. A user is able to communicate the parameter data to a destination such as for storage in repository 17 in response to selection of button 615. A user is able to initiate processing of another image on a patient monitoring device in response to selection of button 617.

In step 222 a user confirms individual parameters and labels in rows 607, 609, 611 and 613 via image elements in the rows in image 603. A user modifies parameters, labels or values in step 225 if necessary, and initiates communication of data representing parameter labels and values to a destination in response to user selection of button 615. Output processor 41 communicates the data representing parameter labels and values for storage in patient record 15 in a healthcare information system in step 231 in response to user selection of button 615.

The system in one embodiment recognizes and interprets graph data by recognizing scales of the axes of a graph and by recognizing a curve in relation to the recognized scales and using the recognized curve and scale data in detecting parameter values at particular times. The system uses an OCR (Optical Character Recognition) function. The OCR function analyzes an image within a masked out area to extract the text and lines, e.g., a graph and scale that is in the image. The system recognizes a particular image of a particular device by matching with predetermined template images or features based on image object comparison using iterative scaling, translation and rotation functions to recognize matching objects and features to identify an image. A library of images (with associated image masks) of devices in different configuration states is used. This includes masks for each of the images which are potentially displayed. An overall image is recognized by matching shape, color and layout, for example, to existing stored masks. Patient monitoring device 27 may also be recognized by an identification tag (a model name, or manufacturer name) on the device. This tag as well is masked out with a special mask known as an identification tag mask.

Information in repository 17 includes a lookup table associating device types and patient monitoring device models and versions with a particular image of multiple different images of a version of an individual patient monitoring device of a particular manufacturer with labels used on the device images (e.g. predetermined labels HR, RR, NIBP, TEMP (TEMPERATURE)) and with predetermined image locations at which labels are shown. In an embodiment, masks employ a Cartesian coordinate system and mask position is displayed as a set of x,y coordinates that make up that mask. In FIG. 3, an identification mask comprises a coordinate square given by corner coordinates {(1,1),(2,1),(2,2),(1,2)} that designates the coordinate square within which processor 43 looks for device identification data specifically labels "ProCare 400™" and "GE®". Coordinate geometrical position is used to identify mask area in an image. The masks may comprise different shapes or complex vectors. There are multiple entries in a mask table stored in repository 17 defining separate different masks (identified by different mask IDs) for multiple different devices.

TABLE I

| Mask ID | Identification tag value | Identification tag mask position | Device Shape, layout, color |
|---|---|---|---|
| 1 | GE ProCare 400 | {(1, 1), (2, 1), (2, 2), (1, 2)} | Store image for image matching |
| 2 | GE ProCare 400 | {(1, 1), (2, 1), (2, 2), (1, 2)} | Store image for image matching |

In Table I the GE ProCare 400™ device has two different stored masks having mask id 1 and mask id 2 and associated with corresponding different images used for different versions of the device but having the same identification tag mask location.

Processor 43 analyzes acquired images to determine if there is an identification tag mask in the specified position and acquires and reads the identification value. The identification value is associated with a Mask ID and different device images associated with the Mask ID are matched to an acquired image of the device to determine the best match image. If there is no matching identification value, an image match is performed to find a similar image and to subsequently determine a mask ID but without a prior mask ID determination, more image matches are likely to be needed to find a best match.

TABLE II

| Mask ID | Mask value | Mask position |
|---|---|---|
| 1 | Sp02 | {(2.5, 2), (3, 2), (2.5, 2.5), 3, 2.5)} |
| 1 | Systolic NIBP | {(2.5, 5), (2.5, 5.75), (4, 5), (4, 5.75)} |

A lookup table in repository 17 such as Table II for example, provides mask coordinates {(2.5,2),(3,2),(2.5,2.5),(3,2.5)} identifying a rectangle in FIG. 3 showing an SPO2 value (99), and coordinates {(2.5,5),(2.5,5.75),(4,5),(4,5.75)} identifying a rectangle showing a systolic pressure value (120).

Figure 8:
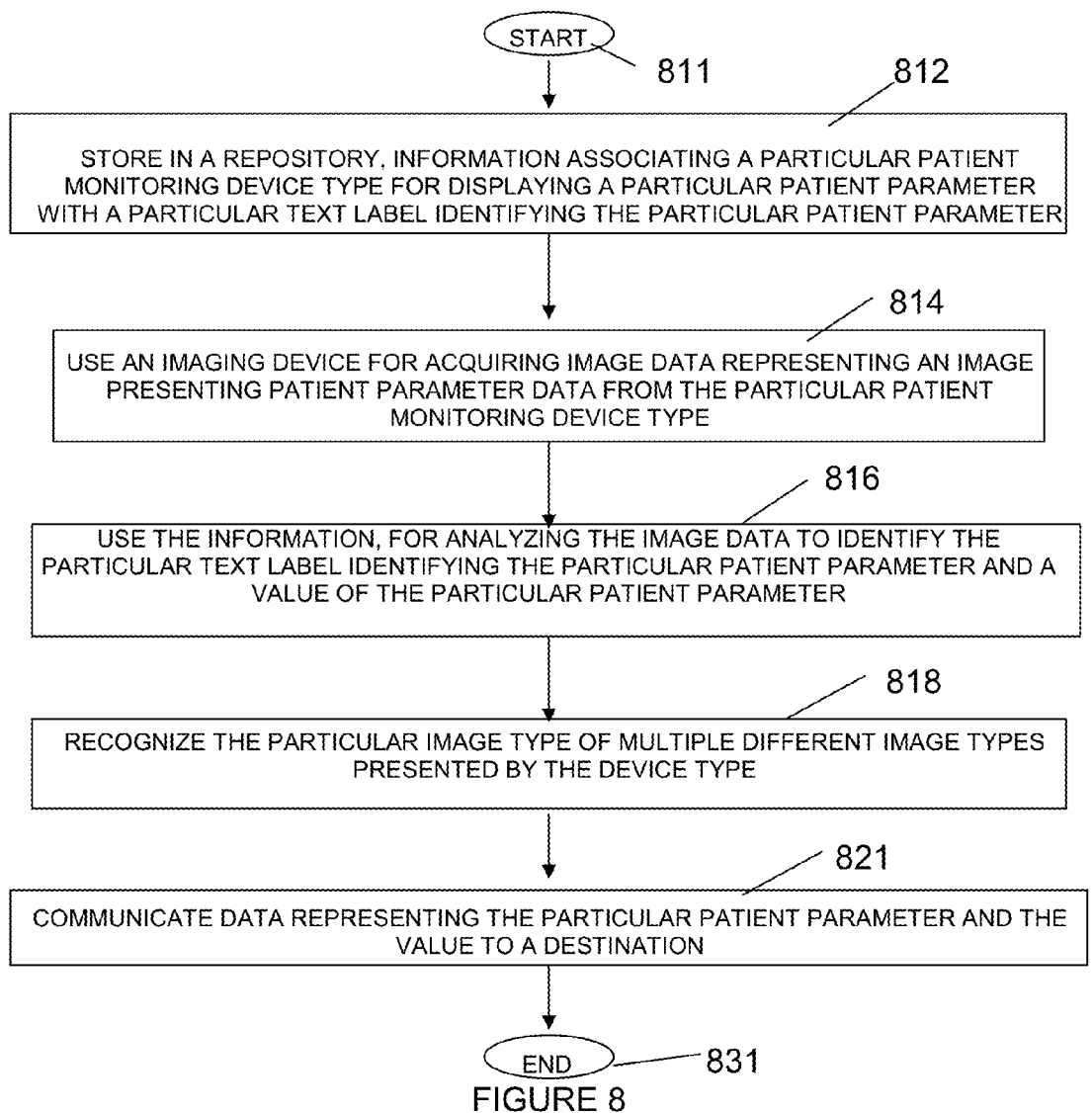
FIG. 8 shows a flowchart of a process used by a mobile processing device system for patient monitoring data acquisition, according to an embodiment of the invention.

FIG. 8 shows a flowchart of a process used by mobile processing device system 10 for patient monitoring data acquisition. In step 812 following the start at step 811, system 10 stores in repository 17, information associating a particular patient monitoring device type for displaying a particular patient parameter with a particular text label identifying the particular patient parameter. The repository of information associates the particular patient monitoring device type with a particular image type displayed by the device type and with a particular text label identifying the particular patient parameter presented in the particular image type and with a mask identifying a particular area within the particular image containing the particular patient parameter and the particular text label. The repository of information also associates the particular patient monitoring device type with a version identifier and a manufacturer identifier and associates the particular patient monitoring device type with particular text labels including at least two of, HR, RR, NIBP, TEMP (TEMPERATURE), for example.

A user in step 814 employs an imaging device (camera 35) of portable processing device 12 for acquiring image data representing an image presenting patient parameter data from the particular patient monitoring device type. In step 816 image recognition processor 43 uses the information, for analyzing the image data to identify the particular text label identifying the particular patient parameter and a value of the particular patient parameter. In step 818, image recognition processor 43 recognizes the particular image type of multiple different image types presented by the device type. Image recognition processor 43 analyzes the image data to identify the particular patient parameter and particular text label by using the mask to identify the particular area within the particular image containing the particular patient parameter and particular text label.

Processor 43 analyzes the image data to recognize the patient parameter value and particular text label in the particular area using at least one of, (a) an optical character recognition method and (b) one or more of image data translation, rotation and scaling operations. In one embodiment, processor 43 analyzes the image data to identify the particular text label using data identifying the version identifier and the manufacturer identifier. Output processor 41 in step 821 communicates data representing the particular patient parameter and the value to a destination. In one embodiment, repository 17, image recognition processor 43 and output processor 41 are within portable processing device 12. Alternatively, repository 17, image recognition processor 43 and output processor 41 are located remotely from portable processing device 12. In one embodiment, the information includes mapping information associating an identified particular patient parameter with a normal value range for a patient having similar demographic characteristics to the patient and image recognition processor 43 validates identification of a label of the particular patient parameter in response to comparison of the identified particular patient parameter with the normal value range. The demographic characteristics comprise at least one of age, weight, gender, height and pregnancy status. The process of FIG. 8 terminates at step 831.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system uses a camera on a mobile device to collect and transcribe vital sign, graph data and other patient data to text. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both. No claim element herein is to be construed under the provisions of 35 U.S.C. 112, sixth paragraph, unless the element is expressly recited using the phrase "means for."

What is claimed is:

1. A mobile processing device system for patient monitoring data acquisition, comprising:
   a repository of information associating a particular patient monitoring device type for displaying a particular patient parameter with a particular image type displayed by said device type and with a particular text label identifying said particular patient parameter in said particular image type;
   a portable processing device including an imaging device for acquiring image data representing an image presenting patient parameter data from the particular patient monitoring device type;
   an image recognition processor, using said information, for analyzing said image data to identify said particular text label identifying said particular patient parameter and a value of said particular patient parameter, and wherein said image recognition processor recognizes said particular image type of a plurality of different images types presented by said device type; and
   an output processor for communicating data representing said particular patient parameter and said value to a destination.

2. The system according to claim 1, wherein
   said repository, said image recognition processor and said output processor are within said portable processing device.

3. The system according to claim 1, wherein
   at least one of, said repository, said image recognition processor and
   said output processor are located remotely from said portable processing device.

4. The system according to claim 1, wherein
   said image recognition processor analyzes said image data to identify
   said particular text label using image data translation, rotation and scaling operations.

5. The system according to claim 1, wherein
   said repository of information further associates said particular patient monitoring device type with a mask identifying a particular area within said particular image containing said particular patient parameter and
   said image recognition processor analyzes said image data to identify said particular patient parameter by using said mask to identify said particular area within said particular image containing said particular patient parameter.

6. The system according to claim 5, wherein
   said image recognition processor analyzes said image data to recognize said patient parameter value in said particular area using at least one of, (a) an optical character recognition method and (b) one or more of image data translation, rotation and scaling operations.

7. The system according to claim 1, wherein
   said repository of information further associates said particular patient monitoring device type with a mask identifying a particular area within said particular image containing said particular text label and
   said image recognition processor analyzes said image data to identify said particular text label by using said mask to identify said particular area within said particular image containing said particular text label.

8. The system according to claim 7, wherein
   said image recognition processor analyzes said image data to recognize said particular text label in said particular area using at least one of, (a) an optical character recognition method and (b) one or more of image data translation, rotation and scaling operations.

9. The system according to claim 1, wherein
said repository of information further associates said particular patient monitoring device type with a version identifier and a manufacturer identifier and
said image recognition processor analyzes said image data to identify said particular text label using data identifying said version identifier and said manufacturer identifier.

10. The system according to claim 1, wherein
said repository of information further associates said particular patient monitoring device type with particular text labels including at least two of, HR, RR, NIBP, TEMP (TEMPERATURE) and
said image recognition processor analyzes said image data to identify at least one of said particular text labels.

11. The system according to claim 1, wherein
said information includes mapping information associating an identified particular patient parameter with a normal value range for a patient having similar demographic characteristics to said patient and
said image recognition processor validates identification of a label of said particular patient parameter in response to comparison of said identified particular patient parameter with said normal value range.

12. The system according to claim 11, wherein
said demographic characteristics comprise at least one of age, weight, gender, height and pregnancy status.

13. A method for acquiring patient monitoring data, comprising the activities of:
storing in a repository, information associating a particular patient monitoring device type for displaying a particular patient parameter with a particular image type displayed by said device type and with a particular text label identifying said particular patient parameter presented in said particular image type and including the activity of recognizing said particular image type of a plurality of different image types presented by said device type;
using an imaging device for acquiring image data representing an image presenting patient parameter data from the particular patient monitoring device type;
using said information, for analyzing said image data to identify said particular text label identifying said particular patient parameter and a value of said particular patient parameter; and
communicating data representing said particular patient parameter and said value to a destination.

14. The method according to claim 13, including the activity of analyzing said image data to identify said particular text label using image data translation, rotation and scaling operations.

15. The method according to claim 13, wherein
said information further associates said particular patient monitoring device type with a mask identifying a particular area within said particular image containing said particular patient parameter and including the activity of
analyzing said image data to identify said particular patient parameter by using said mask to identify said particular area within said particular image containing said particular patient parameter.

16. The method according to claim 15, including the activity of
analyzing said image data to recognize said patient parameter value in said particular area using at least one of, (a) an optical character recognition method and (b) one or more of image data translation, rotation and scaling operations.

17. The method according to claim 13, wherein
said information further associates said particular patient monitoring device type with a mask identifying a particular area within said particular image containing said particular text label and including the activity of
analyzing said image data to identify said particular text label by using said mask to identify said particular area within said particular image containing said particular text label.

18. The method according to claim 17, including the activity of
analyzing said image data to recognize said particular text label in said particular area using at least one of, (a) an optical character recognition method and (b) one or more of image data translation, rotation and scaling operations.

19. The method according to claim 13, wherein
said information further associates said particular patient monitoring device type with a version identifier and a manufacturer identifier and including the activity of
analyzing said image data to identify said particular text label using data identifying said version identifier and said manufacturer identifier.

20. The method according to claim 13, wherein
said information further associates said particular patient monitoring device type with particular text labels including at least two of, HR, RR, NIBP, TEMP (TEMPERATURE) and including the activity of
analyzing said image data to identify at least one of said particular text labels.

\* \* \* \* \*